(12) United States Patent
Lanzoni (10) Patent No.: US 9,192,687 B2
(45) Date of Patent: Nov. 24, 2015

(54) DISINFECTING OR STERILIZING MACHINE FOR DISINFECTING OR STERILIZING ENDOSCOPES

(71) Applicant: ASE S.R.L., Bologna (IT)

(72) Inventor: Marco Lanzoni, Bologna (IT)

(73) Assignee: ASE S.R.L., Bologna (IT)

( * ) Notice: Subject to any disclaimer, the term of this patent is extended or adjusted under 35 U.S.C. 154(b) by 0 days.

(21) Appl. No.: 14/439,744

(22) PCT Filed: Nov. 28, 2013

(86) PCT No.: PCT/IB2013/060467
§ 371 (c)(1),
(2) Date: Apr. 30, 2015

(87) PCT Pub. No.: WO2014/083524
PCT Pub. Date: Jun. 5, 2014

(65) Prior Publication Data
US 2015/0290349 A1 Oct. 15, 2015

(30) Foreign Application Priority Data
Nov. 30, 2012 (IT) .............................. BO2012A0648

(51) Int. Cl.
*A61L 2/18* (2006.01)
*A61L 2/16* (2006.01)
*A61L 2/26* (2006.01)

(52) U.S. Cl.
CPC ... *A61L 2/18* (2013.01); *A61L 2/16* (2013.01); *A61L 2/26* (2013.01); *A61L 2202/24* (2013.01)

(58) Field of Classification Search
CPC ............... A61L 2/16; A61L 2/18; A61L 2/26; A61L 2202/24
USPC ........................................... 422/292, 300, 301
See application file for complete search history.

(56) References Cited

U.S. PATENT DOCUMENTS 7,608,228 B2 * 10/2009 Horacek ............ A61B 19/0271
422/292

FOREIGN PATENT DOCUMENTS

| DE | 195 14 303 A1 | 10/1996 |
| EP | 1 787 731 A2 | 5/2007 |
| WO | WO 02/11602 A2 | 2/2002 |
| WO | WO 2007/000639 A1 | 1/2007 |
| WO | WO 2009/016111 A1 | 2/2009 |

* cited by examiner

*Primary Examiner* — Sean E Conley
(74) *Attorney, Agent, or Firm* — R. Neil Sudol; Henry D. Coleman (57) ABSTRACT

A machine for disinfecting or sterilizing endoscopes comprises a tunnel having a first opening and a second opening, an upper wall delimiting the tunnel, first and second lateral walls respectively positionable at the first and second openings to obstruct the tunnel, a bath for receiving an endoscope, a bath support, a guide for guiding the bath support and the bath along the tunnel between a first endrun and a second endrun, in which the bath projects externally from the first tunnel opening and the second tunnel opening, respectively, to enable endoscope insertion and extraction. The upper wall forms, with the bath, a closed chamber for treating an endoscope when the bath is inside the tunnel. The first and second lateral walls are removably couplable to the frame to selectively obstruct the tunnel or enable the bath support and bath to reach the respective endruns.

13 Claims, 9 Drawing Sheets

DISINFECTING OR STERILIZING MACHINE FOR DISINFECTING OR STERILIZING ENDOSCOPES

FIELD OF THE INVENTION

The present invention relates to the technical sector relating to disinfecting/sterilising machines of rigid and flexible endoscopes.

DESCRIPTION OF THE PRIOR ART

A disinfecting/sterilising machine is known for disinfecting/sterilizing endoscopes which comprises: a frame; a casing covering the frame so as define a tunnel having a first opening and a second opening which is opposite the first opening; an upper wall superiorly delimiting the tunnel; a first lateral wall positioned at the first opening such as to obstruct the tunnel, which first lateral wall is hinged to the frame; a second lateral wall positioned at the second opening such as to obstruct the tunnel, which second lateral wall is hinged to the frame; a basket dimensioned so as to receive one or more endoscopes to be disinfected/sterilized and which is dimensioned so as to transit along the tunnel.

The upper wall, the bottom wall and the first lateral wall and the second lateral wall, when closed, define a closed chamber for disinfecting/sterilizing the endoscope arranged in the basket.

The hinge axis of the first lateral wall is horizontal and arranged at the lower side of the first opening; therefore, the first lateral wall is actionable between a vertical position in which it closes the first opening of the tunnel and a horizontal position in which it makes the tunnel accessible by means of the first opening. Likewise, the hinge axis of the second lateral wall is horizontal and arranged at the lower end of the second opening; therefore the second lateral wall is activatable between a vertical position in which it closes the second opening of the tunnel and a vertical position in which it closes the second opening of the tunnel and a horizontal position in which it makes the tunnel accessible via the second opening.

The basket can be drawn to the outside of the tunnel by sliding on the first lateral wall or on the second lateral wall, which enables the operator to collect a disinfected endoscope from the basket or to leave one to be disinfected/sterilized in the basket.

As is known, a disinfecting/sterilising machine of this type is suitable for inserting in a wall opening fashioned in a wall dividing two different rooms: a first room can be a service room while a second room can be the operating theatre; the first opening can be arranged for example in the service room, while the second opening can be arranged in the operating theatre. An endoscope used on a patient in the operating theatre is then brought by the operator into the service room and inserted in the disinfecting machine through the first opening; once the endoscope has been disinfected in the disinfecting/sterilizing machine it can be collected by an operator in the operating theatre through the second opening.

A drawback of a disinfecting/sterilising machine of this type is the particularly large size thereof; this size is mainly due to the dimensions of the chamber receiving the basket with the endoscope to be disinfected/sterilised; also, it is not possible to reduce the dimensions of the chamber beyond a certain limit, as the basket and the endoscope in turn occupy a volume which cannot be reduced below a certain limit.

This drawback is particularly noted in disinfecting machines having a plurality of chambers (two or even three) for disinfecting/sterilizing a plurality of endoscopes at the same time. These machines develop in height or width and occupy very much space.

SUMMARY OF THE INVENTION

The aim of the present invention consists in obviating the above drawback.

A further aim of the present invention consists in inventing a disinfecting/sterilising machine which enables reducing the number of actions that an operator has to perform in order to insert in the disinfecting/sterilising machine an endoscope to be disinfected/sterilized: in fact, to insert an endoscope to be disinfected/sterilized in a disinfecting/sterilising machine of known type it is necessary to activate the first lateral wall so as to lower it into a horizontal position, extract the empty basked from the tunnel, insert the endoscope to be disinfected/sterilized into the basket, insert the basket with the endoscope in the tunnel and activate the first lateral wall so as to return it into the vertical position, thus closing the chamber; likewise, in order to extract a disinfected endoscope from the disinfecting/sterilizing machines it is necessary to activate the second lateral wall so as to lower it into the horizontal position, extract the basked with the disinfected endoscope from the tunnel, insert the empty basket into the tunnel and activate the second lateral wall so as to return it into the vertical position, thus closing the chamber.

The above aims have been attained by means of a disinfecting/sterilising machine for disinfecting/sterilising endoscopes in accordance with claim 1.

According to the invention, in order to insert an endoscope to be disinfected/sterilised into the disinfecting/sterilising machine it is sufficient to extract the bath from the tunnel (for example by transiting it through the first opening), insert the endoscope to be disinfected/sterilised into the bath and insert the bath containing the endoscope into the tunnel; likewise, to extract a disinfected endoscope from the disinfecting/sterilising machine it is sufficient to extract the bath containing the endoscope disinfected from the tunnel (for example by transiting the bath through the second opening), extracting the disinfected endoscope from the bath and inserting the empty bath into the tunnel. These inserting operations of an endoscope to be disinfected/sterilized into the disinfecting/sterilizing machine and extracting operations of a disinfected endoscope from the disinfecting/sterilizing machine are advantageously more rapid.

A first assembly formed by the first lateral wall, the bath and the bath support can resemble a drawer that is extractable from a frame; this enables for example inserting an endoscope to be disinfected/sterilized into the bath with a smaller number of actions by the operator and therefore more rapidly; likewise, a second assembly formed by the second lateral wall, the bath and the bath support might bring to mind a drawer that is extractable from a frame, which enables, for example, extracting from the bath a disinfected endoscope with a smaller number of actions by the operator and therefore more rapidly.

The disinfecting/sterilising machine of the present invention comprises a unit comprising in turn the first lateral wall, the second lateral wall, the bath, the bath support, the guide means and cleaning means for washing and disinfecting/sterilising and endoscope contained in the chamber; obviously it is possible to include further units that are identical to the above-mentioned unit and arranged on a plurality of levels. It has been observed that a machine according to the present invention and having two levels (and therefore two distinct chambers for sterilising endoscopes) advantageously occupies the same space as a machine of known type of the above-described types and having one chamber only.

Of great importance is also the fact that with the present invention it is possible to predisposed the disinfecting/sterilising machine in such a way that: when the bath projects from the first opening for the purpose of the inserting, for example from the service room, of an endoscope to be disinfected/sterilized, the second lateral wall obstructs the second opening and is anchored to the frame, making the bath inaccessible or in any case the tunnel inaccessible by another operator who is in the operating theatre; when the bath projects from the second opening for the purposes of extraction, from the operating theatre, of a disinfected endoscope, the first lateral wall obstructs the first opening and is anchored to the frame, making the bath or in any case the tunnel inaccessible by another operator who is in the service room. Advantageously it is possible to prevent an operator from injuring her or himself by accidentally touching electrical or mechanical parts arranged in the tunnel.

BRIEF DESCRIPTION OF THE DRAWINGS

Specific embodiments of the invention will be described in the following part of the present description, according to what is set down in the claims and with the aid of the appended tables of drawings, in which:

DESCRIPTION OF PREFERRED EMBODIMENTS

With reference to the appended figures of the drawings, 1 denotes in its entirety a disinfecting/sterilising machine (1) for disinfecting/sterilising endoscopes, object of the present invention, comprising: a frame (2) (FIG. 3); a casing (3) covering the frame (2); the frame (2) and the casing (3) being conformed with regard to one another such as to define at least a tunnel (4) having a first opening (5) and a second opening (6) which is opposite the first opening (5); an upper wall (7) which at least partially superiorly delimits the tunnel (4); a first lateral wall (11) positionable at the first opening (5) such as to obstruct the tunnel (4); a second lateral wall (12) positionable at the second opening (6) such as to obstruct the tunnel (4); a bath (9) dimensioned such as to receive at least an endoscope (not illustrated) to disinfect/sterilise and which is dimensioned such as to transit along the tunnel (4); a bath support (10) fixed to the bath (9), the bath support (10) and the bath (9) forming a bath group (9, 10); guide means (8) for guiding the bath group (9, 10) comprising the bath support (10) and the bath (9) along the tunnel (4) between: a first endrun (A1) in which the bath (9) projects externally from the first opening (5) of the tunnel (4) such as to be accessible for inserting or extracting the at least an endoscope; and a second endrun (A2) in which the bath (9) projects externally from the second opening (6) of the tunnel (4) such as to be accessible such as to insert or extract the at least an endoscope.

The upper wall (7) forms, with the bath (9), a closed chamber (13) such as to disinfect/sterilise the at least an endoscope when the bath (9) is internal of the tunnel (4).

The first lateral wall (11), when at the first opening (5), is couplable alternatively and removably: with the frame (2), such as to be solidly constrained to the frame (2) and obstruct the tunnel (4); or with the bath support (10) such as to be solidly constrained to and be drawn by the bath group (9, 10) and enable the bath group (9, 10) to reach the first endrun (A1).

The second lateral wall (12), when at the second opening (6), is alternatively and removably couplable: with the frame (2), such as to be solidly constrained to the frame (2) and obstruct the tunnel (4); or with the bath support (10) such as to be solidly constrained to and be drawn by the bath group (9, 10) and enable the bath group (9, 10) (9, 10) to reach the second endrun (A2).

The upper wall (7) is solidly constrained to the frame (2).

The disinfecting/sterilising machine (1) further comprises cleaning means (36) for washing and disinfecting/sterilizing an endoscope contained in the chamber (13) when the bath group (9, 10) is in the tunnel (4); the cleaning means (36) are generally of known type and can comprise a hydraulic circuit (not represented) which communicates with the chamber (13), for example by means of hydraulic conduits (37) which open into the upper wall (7) and/or in the bath (9), and which makes it possible to wash and sterilize an endoscope arranged in the bath (9). The cleaning means (36) can comprise also a supply of water (obtainable for example by a connection to the municipal water supply or by means of a tank integrated in the disinfecting/sterilizing machine (1)), in order to perform one or more washing cycles repeatedly causing water to flow into the chamber (13) and the hydraulic circuit, with a final expulsion through a discharge (not illustrated); further, the cleaning means (36) can comprise a supply of liquid disinfectant (for example from an tank integrated into the disinfecting/sterilizing machine) so as to perform one or more washing cycles by repeatedly causing the liquid disinfectant into the chamber (13) and the hydraulic circuit, with a final emulsion through the discharge.

The disinfecting/sterilizing machine (1) is suitable for inserting in a wall opening (27) fashioned in a wall (28), which divides two different environments: a first environment (29) (FIGS. 2, 5) can be a service room (29) while a second environment (30) (FIGS. 2, 5) can be the operating theatre (30); the first opening (5) can be arranged for example in the service room (29), while the second opening (6) can be arranged in the operating theatre (30). An endoscope used on a patient in the operating theatre (30) is successively brought by the operator into the service room (29) and inserted in the disinfecting/sterilizing machine (1) through the first opening (5); once the endoscope has been disinfected in the disinfecting/sterilizing machine (1) it can be collected by an operator in the operating theatre (30) through the second opening (6).

Figure 1:
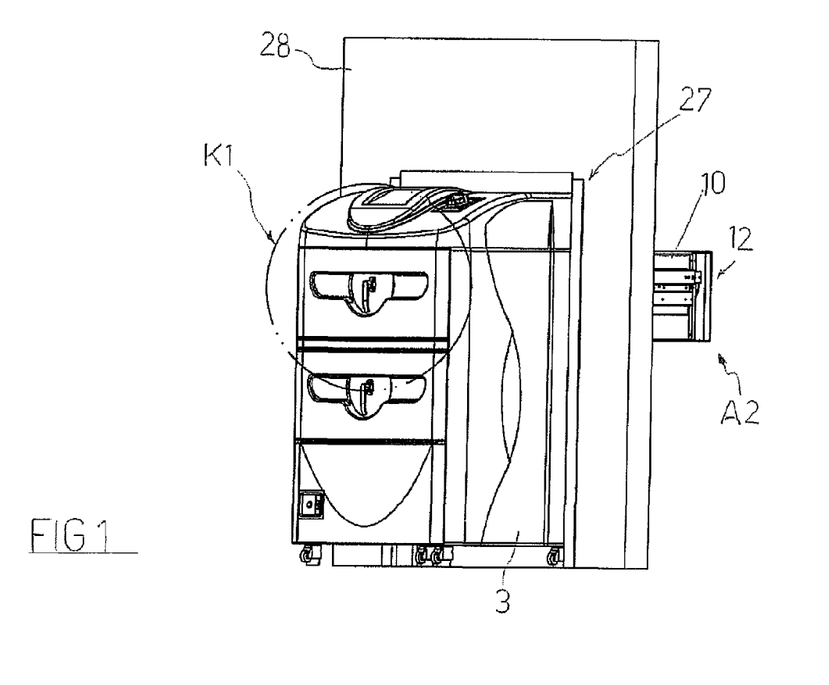
FIGS. 1, 2 are respectively a perspective view and a lateral view of a disinfecting/sterilising machine according to a first embodiment of the present invention, in a first service configuration.

In the appended figures only a part of the wall (28) is shown, for the sake of simplicity; in FIG. 1, in particular, this partial representation of the wall (28) has enabled clearly illustrating the position that the bath group (9, 10) has assumed once it has reached the second endrun (A2).

In the description that follows the insertion and extraction of the bath group (9, 10) into and from the tunnel (4) is done manually, with reference to FIGS. 1, 1A, 2, 3, 4, 4A, 5.

The disinfecting/sterilising machine (1) can further comprise: a first mechanism (14) borne by the first lateral wall (11) and activatable, when the first lateral wall (11) is at the first opening (5), between a first operative configuration (B1) in which it interacts with the frame (2) such as to anchor the first lateral wall (11) to the frame (2) (FIGS. 1, 1A, 2), and a second operative configuration (B2) (FIGS. 4, 4A, 5), in which it interacts with the bath support (10) such as to anchor the first lateral wall (11) to the bath support (10) when the bath group (9, 10) is in the tunnel (4); a first handle (15) which is borne by the first lateral wall (11), which is rotatable between a first angular position (C1) and a second angular position (C2) and which is couplable to the first mechanism (14) such that when the first handle (15) is activated into the first angular position (C1), the first mechanism (14) reaches the first operative configuration (B1), and when the first handle (15) is activated into the second angular position (C2), the first mechanism (14) reaches the second operative configuration (B2).

Figure 4:
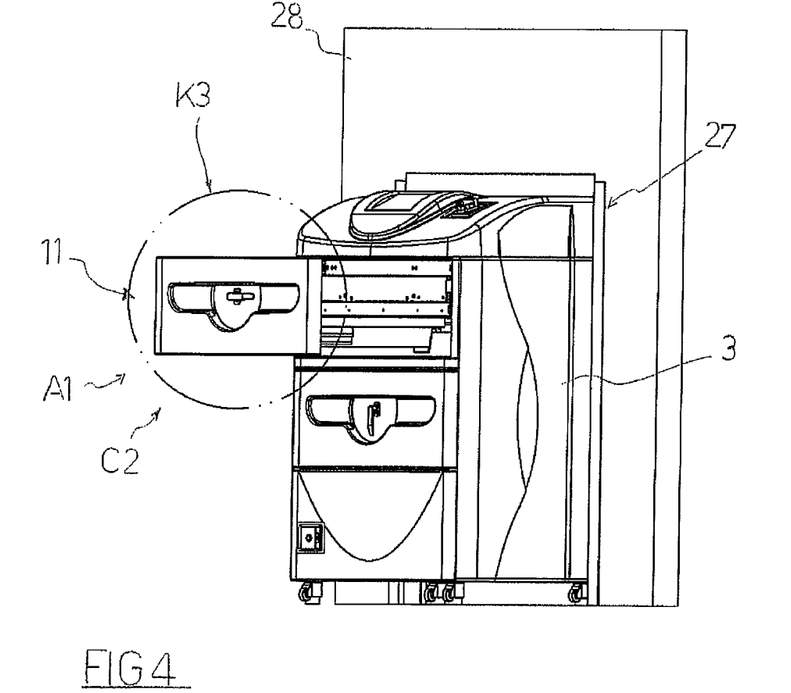
FIGS. 4,5 are respectively a perspective view and a lateral view of the disinfecting/sterilising machine of FIGS. 1-2, in a third service configuration.
Figure 5:
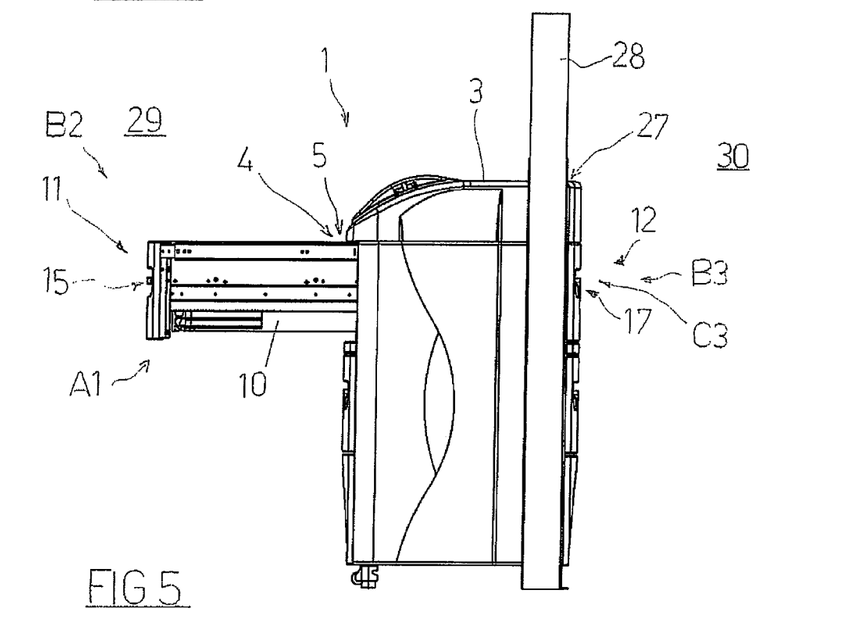
Figure 6:
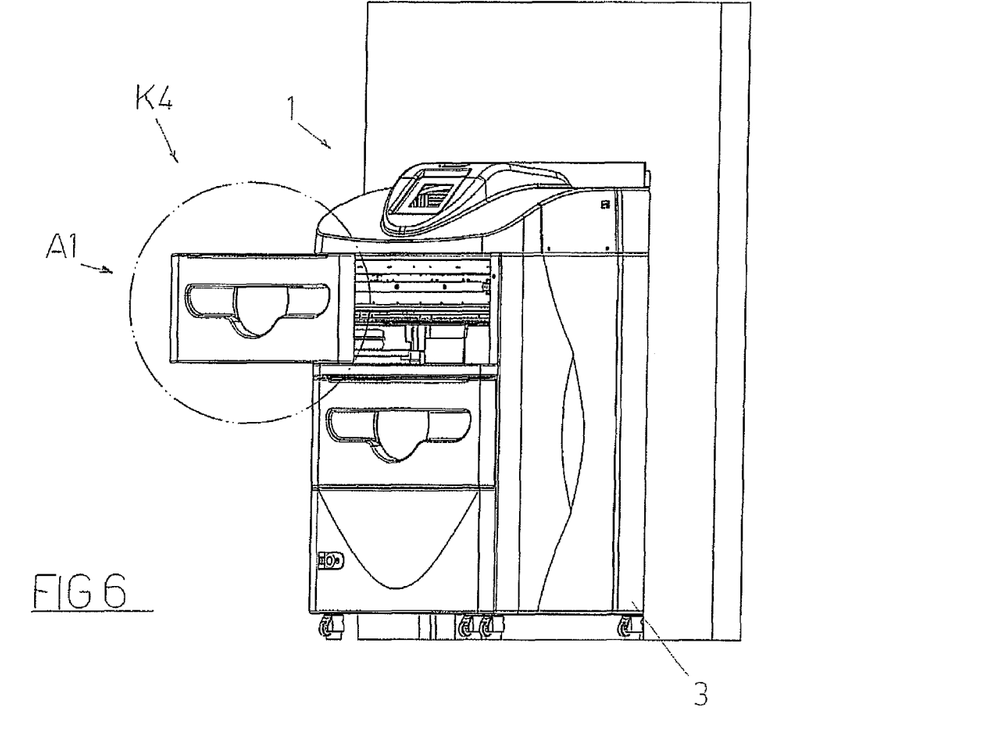
FIG. 6 is a perspective view of a disinfecting/sterilizing machine according to a second embodiment of the present invention, when it is in the third service configuration.
Figure 6A:
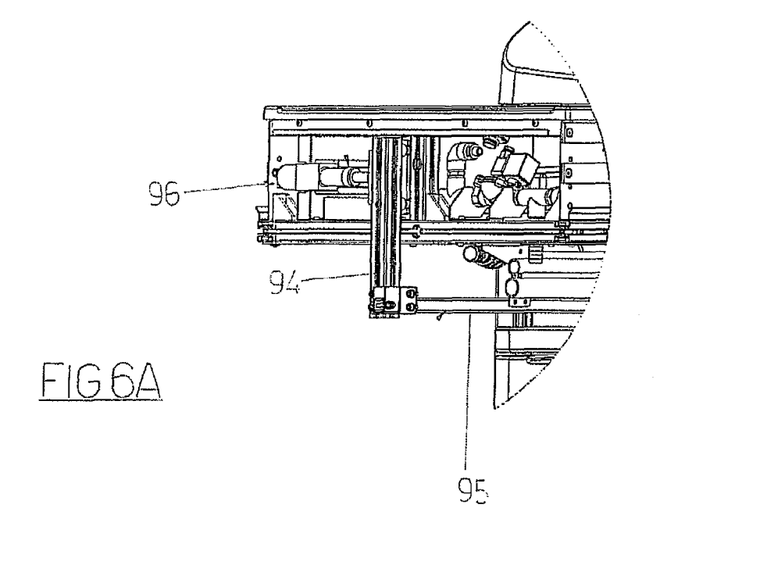
FIG. 6A is a larger-scale view of detail K4 of FIG. 6, where some parts have been removed better to represent others.
Figure 7:
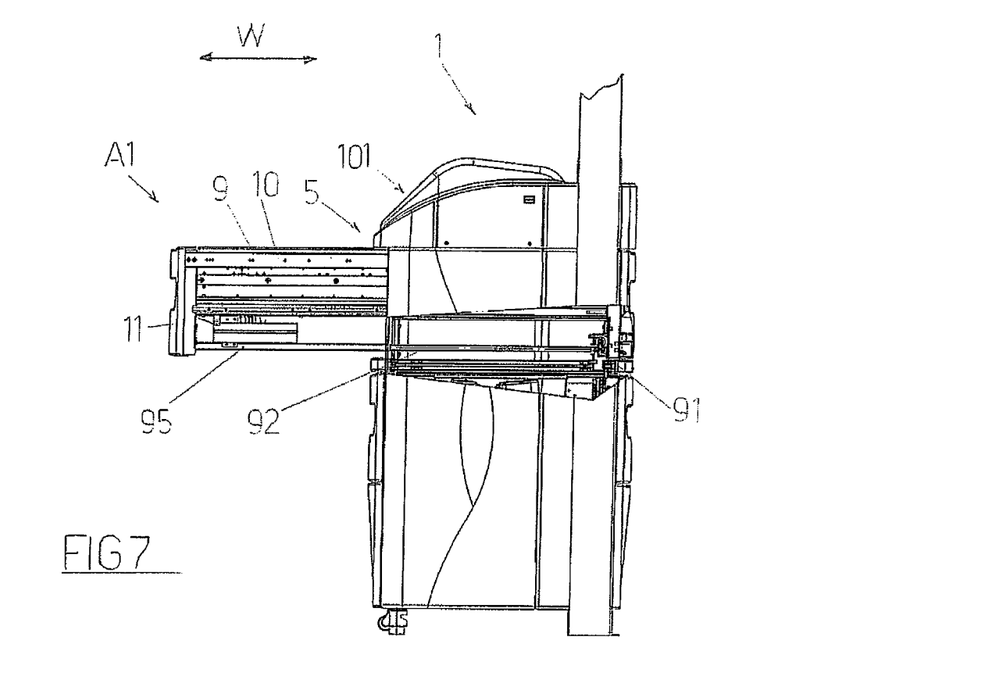
FIG. 7 is a lateral view of the disinfecting/sterilising machine of FIG. 6, where some parts have been removed better to represent others.

In this way an operator who is in the service room (29) can act on the first handle (15) in order to removably couple the first lateral wall (11) to the frame (2) or to the bath support (10); in the last case he can also extract the bath (9) to as to bring the bath group (9, 10) into the first endrun (A1) and insert, for example, an endoscope to be disinfected/sterilized in the bath (9) (FIGS. 4, 5).

The disinfecting/sterilising machine (1) can further comprise: a second mechanism (16) borne by the second lateral wall (12) and activatable, when the second lateral wall (12) is at the second opening (6), between a third operative configuration (B3) (FIG. 5), in which it interacts with the frame (2) such as to anchor the second lateral wall (12) to the frame (2), and a fourth operative configuration (B4) (FIG. 2), in which it interacts with the bath support (10) such as to anchor the second lateral wall (12) to the bath support (10) when the bath group (9, 10) is in the tunnel (4); a second handle (17) which is borne by the second lateral wall (12), which is rotatable between a third angular position (C3) and a fourth angular position (C4) and which is couplable to the second mechanism (16) such that when the second handle (17) is activated into the third angular position (C3) the second mechanism (16) reaches the third operative configuration (B3) and when the second handle (17) is activated into the fourth angular position (C4) the second mechanism (16) reaches the fourth operative configuration (B4).

In this way an operator in the operating theatre (30) can act on the second handle (17) so as to removably couple the second lateral wall (12) to the frame (2) or to the bath support (10); in the last case he can also extract the bath (9) so as to bring the bath group (9, 10) into the second endrun (A2) and so as to extract for example an endoscope disinfected by the bath (9).

The first handle (15) and the first mechanism (14) are preferably at a side of the first lateral wall (11) which is opposite the side in which the bath group (9, 10) is situated; the first lateral wall (11) affords a first through-hole (21); the bath support (10) bears a first projecting element (31) having a first head (41), which first projecting element (31) is dimensioned such as to be inserted through the first through-hole (21) and such as to project therefrom by the first head (41) when the bath group (9, 10) (9, 10) is in the tunnel (4) and the first lateral wall (11) is at the first opening (5); the first mechanism (14) comprises: a first member (18) fixed to the first handle (15), which first member (18) forms a first coupling seating (45) which engages with the first head (41) of the first projecting element (31) when the first handle (15) is in the second angular position (C2), when the first lateral wall (11) is at the first opening (5) and when the bath group (9, 10) is in the tunnel (4), determining the anchoring of the first lateral wall (11) to the bath support (10).

The first mechanism (14) preferably comprises a first latch (19) activatable between an advanced position (D1) and a retracted position (D2) following the movement of the first handle (15) respectively between the first angular position (C1) and the second angular position (C2); the frame (2) comprises a first blocking seating (not illustrated) for receiving the first latch (19) when the first latch (19) reaches the advanced position (D1) and when the first lateral wall (11) is at the first opening (5), with a consequent anchoring of the first lateral wall (11) to the frame (2).

The first latch (19) can comprise a first guide support (51) fixed to the first lateral wall (11) and a first rod (61) which can slide guided by the first guide support (51); a first end of the first rod (61) can engage in the first blocking seating. The first mechanism (14) can further comprise a first arm (71) which is hinged at an end thereof to a second end of the first rod (61) which is opposite the first end of the first rod (61).

The second handle (17) and the second mechanism (16) are preferably on a side of the second lateral wall (12) which is opposite the side at which the bath group (9, 10) is situated; the second lateral wall (12) affords a second through-hole (not illustrated); the bath support (10) bears a second projecting element (32) having a second head (42), which second projecting element (32) is dimensioned such as to be inserted through the second through-hole and such as to project therefrom by the second head (42) when the bath group (9, 10) (9, 10) is in the tunnel (4) and the second lateral wall (12) is at the second opening (6); the second mechanism (16) comprises: a second member (18) (not visible in the figures) fixed to the second handle (17), which second member forms a second coupling seating (not visible in the figures) which engages with the second head (42) of the second projecting element (32) when the second handle (17) is in the fourth angular position (C4), when the second lateral wall (12) is at the second opening (6) and when the bath group (9, 10) (9, 10) is in the tunnel (4), determining the anchoring of the second lateral wall (11) to the bath support (10).

The second mechanism (16) further preferably comprises: a second latch (not visible in the figures) activatable between an advanced position (D1) and a retracted position (D2) following the movement of the second handle (17) respectively between the third angular position (C3) and the fourth angular position (C4); the frame (2) comprises a second blocking seating (not visible in the figures) for receiving the second latch when the second latch reaches the advanced position (D1) and when the second lateral wall (12) is at the second opening (6), with a consequent anchoring of the second lateral wall (12) to the frame (2).

The second latch (19) can comprise a second guide support (not illustrated) fixed to the first lateral wall (11) and a second rod (not illustrated) which can slide guided by the second guide support; a first end of the second rod can engage in the second blocking seating. The second mechanism (16) can further comprise a second arm (not illustrated) which is hinged at an end thereof to a second end of the second rod which is opposite the first end of the second rod.

The disinfecting/sterilising machine (1) preferably comprises a seal (26) (FIG. 3A) which: is borne by the upper wall (7); develops in a closed loop such as to face the perimeter edge of the bath (9) when the bath (9) is in the tunnel (4); has a tubular transversal section (FIG. 3A) for containing a pressurised fluid; is made of a material which enables the seal (26) to expand or retract according to the fluid pressure contained internally thereof; is dimensioned such that when it expands and when the bath (9) is in the tunnel (4) the chamber (13) is hermetically closed; is dimensioned such that when it retracts the bath group (9, 10) can transit freely through the tunnel (4).

When the seal (26) expands or retracts, the transversal section of the seal (26) increases or reduces respectively; in other words when the seal (26) is inflated it expands and when it is deflated it retracts.

Figure 1A:
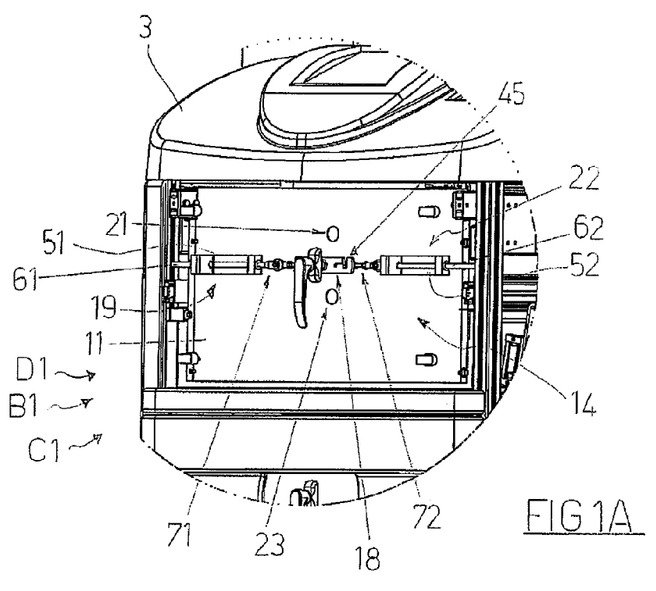
FIG. 1A is a larger-scale view of detail K1 of FIG. 1, where some parts have been removed better to represent others.
Figure 2:
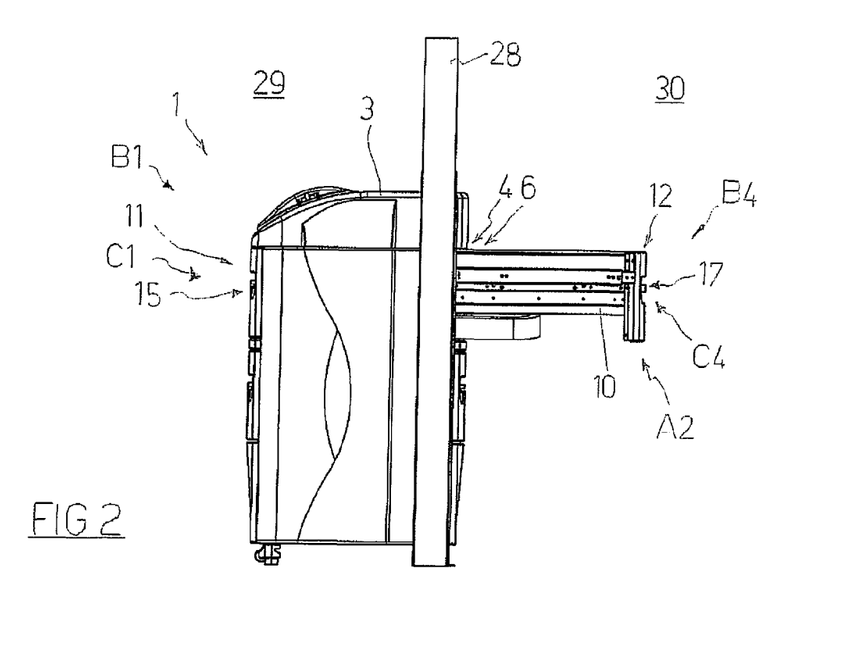

FIGS. 1, 1A, 2 illustrate the disinfecting/sterilising machine (1) in a first service configuration, which is described in the following.

The first lateral wall (11) is positioned at the first opening (5) for obstructing the tunnel (4) and is removably coupled with the frame (2); the first handle (15) is in the first angular position (C1), the first mechanism (14) is in the first operative configuration (B1) and the first latch (19) is in the advanced position (D1) and engages with the first blocking seating for anchoring the first lateral wall (11) to the frame (2). The bath group (9, 10) is in the second endrun (A2) and therefore projects from the second opening (6) in order to made the bath (9) accessible by an operator who is in the operating theatre (30), which operator for example can extract a disinfected endoscope from the bath (9). The second lateral wall (12) is coupled to the bath support (10) and is solidly constrained thereto; the second handle (17) is in the fourth operative configuration (C4), the second mechanism (16) is in the fourth operative configuration (B4) and the second latch is in the retracted position (D2).

In the first service configuration the first lateral wall (11) obstructs the tunnel (4) and prevents an operator in the service room (29) from accessing the tunnel (4), with the risk of coming into contact with mechanical and/or electrical components.

The disinfecting/sterilising machine (1) can further comprise first admittance means (not illustrated) which unblock the first handle (15) from the first angular position (C1) only when the bath group (9, 10) has reached the tunnel (4) and the second handle (17) has been brought into the third angular position (C3) so as to anchor the second lateral wall (12) to the frame (2); the same effect can be obtained with a first independent activation (not illustrated) such that when the first handle (15) has reached the first angular position (C1) it blocks the first lateral wall (11) to the frame (2) until the bath group (9, 10) has reached the tunnel (4) and the second handle (17) has been brought from the fourth angular position (C4) to the third angular position (C3) so as to anchor the second lateral wall ((12) to the frame (2). The first admittance means or the first independent activation might be commanded by a control unit (not illustrated) that is a part of the disinfecting/sterilising machine (1) of the invention. That would make the disinfecting/sterilising machine even more secure.

Figures 3, 3A:
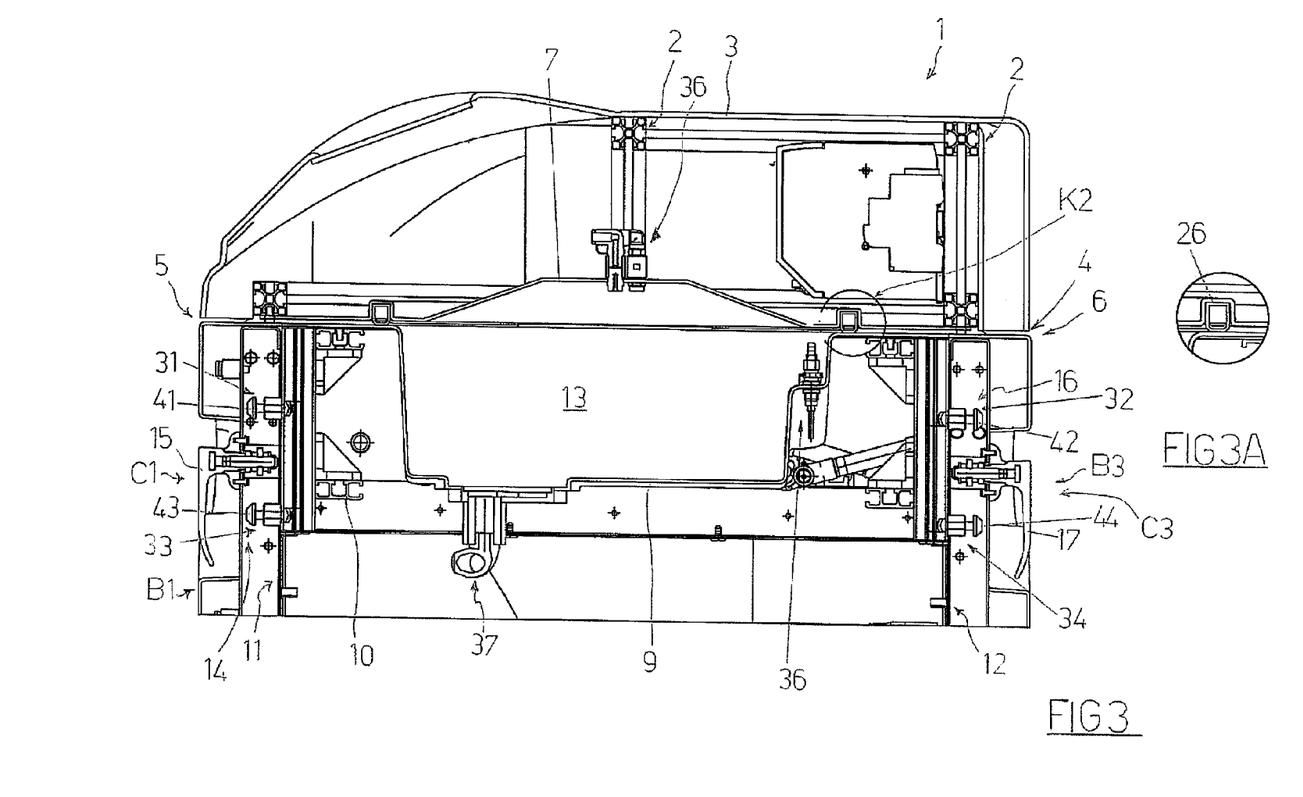
FIG. 3 is a partial view of a transversal section of the machine of FIGS. 1-2 in a second service configuration.
FIG. 3A is a larger-scale view of detail K2 of FIG. 3.

Once the disinfected endoscope has been removed from the operating theatre (30) the operator can manually slide the bath group (9, 10) towards the tunnel (4) until the bath group (9, 10) has reached the tunnel (4) and the second lateral wall (12) has obstructed the second opening (6); thereafter the operator can rotate the second handle (17) so as to bring it into the third angular position (C3) so that the second lateral wall (12) is anchored to the frame (2). This second service configuration of the disinfecting/sterilizing machine is illustrated in FIGS. 3, 3A.

At this point, as mentioned, the first handle (15) can be activated by an operator in the service room (29), into the second angular position (C2) so that the first lateral wall (11) anchors the bath support (10) and the bath group (9, 10) can be brought into the first endrun (A1) so as to insert an endoscope to be sterilised into the bath (9); see FIGS. 4 and 5.

Figure 4A:
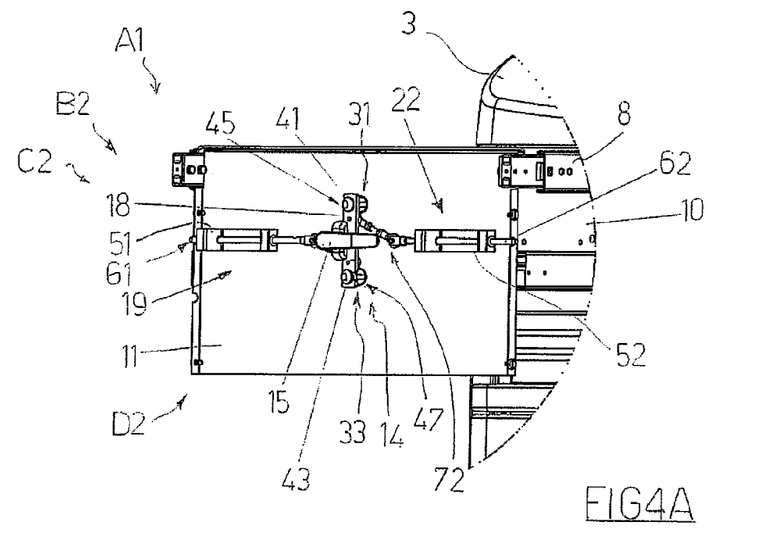
FIG. 4A is a larger-scale view of detail K3 of FIG. 4, where some parts have been removed better to represent others.

FIGS. 4, 4A, 5 illustrate the disinfecting/sterilising machine (1) in a third service configuration, which is described in the following. The second lateral wall (12) is positioned at the second opening (6) so as to obstruct the tunnel (4) and is removably coupled with the frame (2); the second handle (17) is in the third angular position (C3), the second mechanism (16) is in the third operating configuration (B3) and the second latch is in the advanced position (D1) and engages with the second blocking seating so as to anchor the second lateral wall (12) to the frame (2). The bath group (9, 10) is an the first endrun (A1) and therefore projects from the first opening (5) so as to make the bath (9) accessible by an operator who is in the service room (29), which operator for example can place an endoscope to be disinfected/sterilized in the bath (9). The first lateral wall (11) is coupled with the bath support (10) and is solidly constrained thereto; the first handle (15) is in the second angular position (C2), the first mechanism (14) is in the second operating configuration (B2) and the first latch (19) is in the retracted position (D2).

The disinfecting/sterilising machine (1) can additionally comprise second admittance means (not illustrated) which unblock the second handle (17) from the third angular position (C3) only when the bath group (9, 10) has reached the tunnel (4) and the first handle (15) has been brought into the first angular position (C1) so as to anchor the first lateral wall (11) to the frame (2); the same effect can be obtained with a second independent activation (not illustrated) such that when the second handle (17) has reached the third angular position (C3) it blocks the second lateral wall (12) to the frame (2) until the bath group (9, 10) has reached the tunnel (4) and the first handle (15) has been brought from the second angular position (C2) to the first angular position (C1) so as to anchor the first lateral wall (11) to the frame (2). The second admittance means or the second independent activation might be commanded by a control unit (not illustrated, as it is the same as the one already mentioned herein above) that is a part of the disinfecting/sterilising machine (1) of the invention. This would make the disinfecting/sterilising machine even more secure.

Once the disinfected endoscope has been removed from the operating theatre (30) the operator in the service room (29) can manually slide the bath group (9, 10) towards the tunnel (4) until the bath group (9, 10) has reached the tunnel (4) and the first lateral wall (11) has obstructed the first opening (6); thereafter the operator can rotate the first handle (15) so as to bring the it into the first angular position (C1) so that the first lateral wall (11) is anchored to the frame (2).

The disinfecting/sterilising machine (1) is now newly in the second service configuration (FIG. 3, 3A); at this point the seal (26) is inflated to seal the chamber (13) and the cleaning means (36) can be activated to wash and disinfect/sterilize the endoscope contained in the chamber (13). During this process the seal (26) does not allow sliding of the bath group (9, 10); however, the first admittance means and the second admittance means can for example respective unblock the first handle (15) and the second handle (17) only at the end of the washing and disinfection/sterilization of the endoscope, following the receiving of corresponding signals from the control unit. In this way an operator can interfere with the washing and disinfection/sterilization of the endoscope by acting on the first handle (15) or on the second handle (17).

The disinfecting/sterilising machine (1) therefore includes a first unit in turn comprising: the first lateral wall (11), the second lateral wall (12), the bath (9), the bath support (10), the guide means (8) and the cleaning means (36); it is obviously possible to include further identical units to the first unit as described above and arranged on various levels. In the illustrated example the disinfecting/sterilising machine comprises two units arranged on two levels, which can occupy the same space as a disinfecting/sterilising machine (1) of known type, as described in the preamble and having one chamber (13) only.

In an embodiment shown in the accompanying figures, the first lateral wall (11) can afford a third through-hole (23); the bath support (10) can bear a third projecting element (33) having a third head (43), which third projecting element (33) is dimensioned so as to insert through the third through hole (23) and to project therefrom by means of the third head (43) when the bath group (9, 10) is in the tunnel (4) and the first lateral wall (11) is at the first opening (5); the first member (18) can form a third coupling seating (47) which engages with the third head (43) of the third projecting element (33) when the first handle (15) is in the second angular position (C2), when the first lateral wall (11) is at the first opening (5) and when the bath group (9, 10) is in the tunnel (4), determining a stabler anchoring of the first lateral wall (11) to the bath support (10). In addition, the first mechanism (14) further comprises a third latch (22) activatable between an advanced position (D1) and a retracted position (D2) following the movement of the first handle (15) respectively between the first angular position (C1) and the second angular position (C2); the frame (2) comprises a third blocking seating (not illustrated) for receiving the third latch (22) when the third latch (22) reaches the advanced position (D1) and when the first lateral wall (11) is at the first opening (5) with a consequent even stabler anchoring of the first lateral wall (11) to the frame (2).

The third latch (22) can comprise a third guide support (52) fixed to the first lateral wall (11) and a third rod (62) which can slide guided by the third guide support (52); a first end of the third rod (62) can engage in the third blocking seating. The first mechanism (14) can further comprise a third arm (72) which is hinged, at an end thereof, to the first member (18) which is hinged, at the opposite end, to a second end of the third rod (62) that is opposite the first end of the third rod (62).

Likewise, the second lateral wall (12) can exhibit a fourth through-hole (not illustrated); the bath support (10) can bear a fourth projecting element (34) (not illustrated) having a fourth head (44), which fourth projecting element (34) is dimensioned so as to insert through the fourth through-hole and to project therefrom by means of the fourth head (44) when the bath group (9, 10) is in the tunnel (4) and the second lateral wall (12) is at the second opening (6); the second member can form a fourth coupling seating (not illustrated) which engages with the fourth head (44) of the fourth projecting element (34) when the second handle (17) is in the fourth angular position (C4), when the second lateral wall (12) is at the second opening (6) and when the bath group (9, 10) is in the tunnel (4), determining a stabler anchoring of the second lateral wall (11) to the bath support (10). In addition, the second mechanism (16) further comprises a fourth latch (not illustrated) activatable between an advanced position (D1) and a retracted position (D2) following the movement of the second handle (17) respectively between the third angular position (C3) and the fourth angular position (C4); the frame (2) comprises a fourth blocking seating (not illustrated) for receiving the fourth latch when the fourth latch reaches the advanced position (D1) and when the second lateral wall (12) is at the second opening (6) with a consequent even stabler anchoring of the second lateral wall (12) to the frame (2).

The fourth latch can comprise a fourth guide support (not illustrated) fixed to the second lateral wall (12) and a fourth rod (not illustrated) which can slide guided by the fourth guide support; a first end of the fourth rod can engage in the fourth blocking seating. The second mechanism (16) can further comprise a fourth arm (not illustrated) which is hinged, at an end thereof, to the second member and which is hinged, at the opposite end, to a second end of the fourth rod (62) that is opposite the first end of the fourth rod In the above description the insertion and extraction of the bath group (9, 10) into and from the tunnel (4) is done manually, by means of the first mechanism (14), the first handle (15), the second mechanism (16), the second handle (17), etc.

In the description that now follows, the insertion and extraction of the bath group (9, 10) into and from the tunnel (4) is done by an electrical command; reference is made to FIGS. 6, 6A, 7, 8, 9, 10, 10A, 11, 11A. In the above figures and the description that follows identical characteristics to those already mentioned above will be referred-to using the same reference numbers.

The disinfecting/sterilising machine can therefore comprise: a first motor (91) which is borne by the frame (2); a first screw (92) which is drawn in rotation by the first motor (91); a first nutscrew (93) which engages helically with the first screw (92) so as to translate along the first screw (92); a first connecting member (94, 94) which connects the first nutscrew (93) with the first lateral wall (11); first fixing means (96, 97, 98) for removably fixing the first lateral wall (11) to the bath group (9, 10) when the first lateral wall (11) is at the first opening (5) and the bath group (9, 10) is in the tunnel (4), the first motor (91), the first screw (92), the first nutscrew (93) and the first connecting member (94, 95) being dimensioned and arranged with respect to one another so as to enable the bath group (9, 10) to reach the first endrun (A1).

The first bath group (9, 10) slides along a sliding direction (W). The first screw (92) is preferably orientated parallel to the sliding direction (W).

The first connecting member (94, 95) can comprise: a first upright (94) which is fixed to the first lateral wall (11); and a first tubular element (95) which is fixed at a first end to the first upright (94) and which at a second end is fixed to the first nutscrew (93), which first tubular element (95) is concentric with the first screw (92) and is dimensioned such as to at least partly contain the first screw (92) internally thereof.

Figure 8:
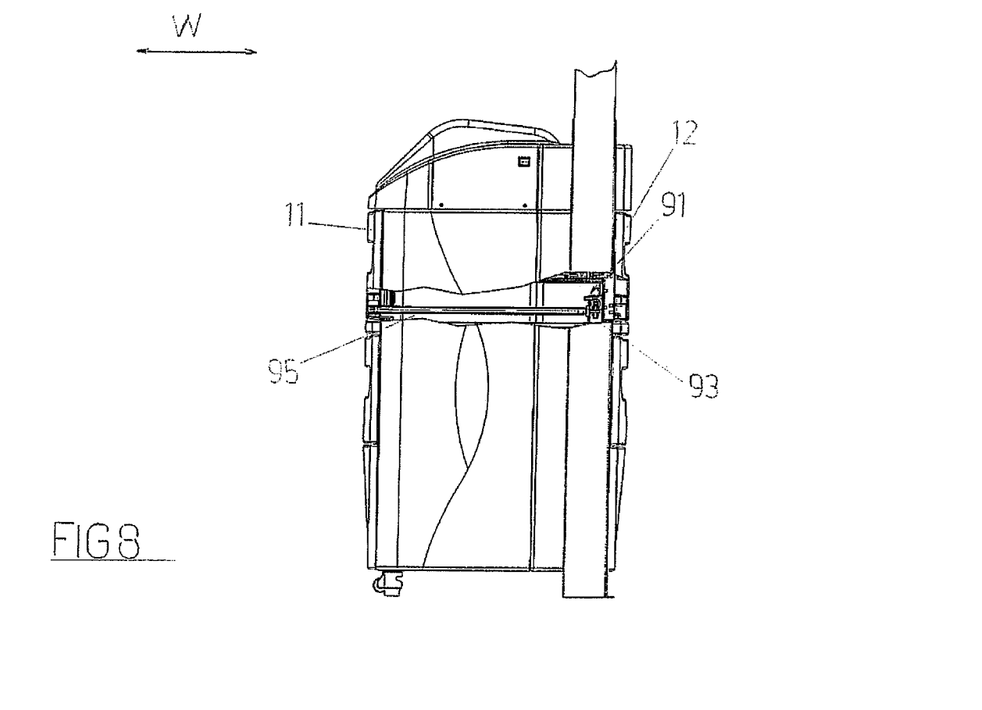
FIG. 8 is a lateral view of the disinfecting/sterilising machine of FIG. 6 when it is in the second service configuration, where some parts have been removed better to represent others.
Figure 9:
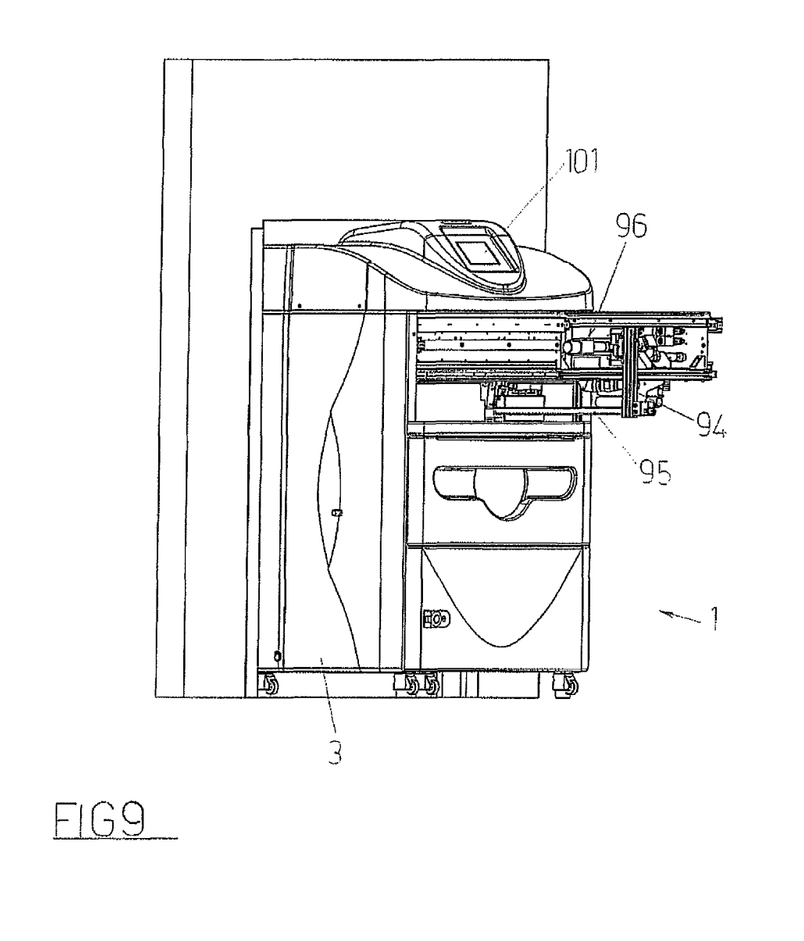
FIG. 9 is a view of the disinfecting/sterilising machine of FIG. 6 from a different perspective and where some parts have been removed better to represent others.
Figure 10:
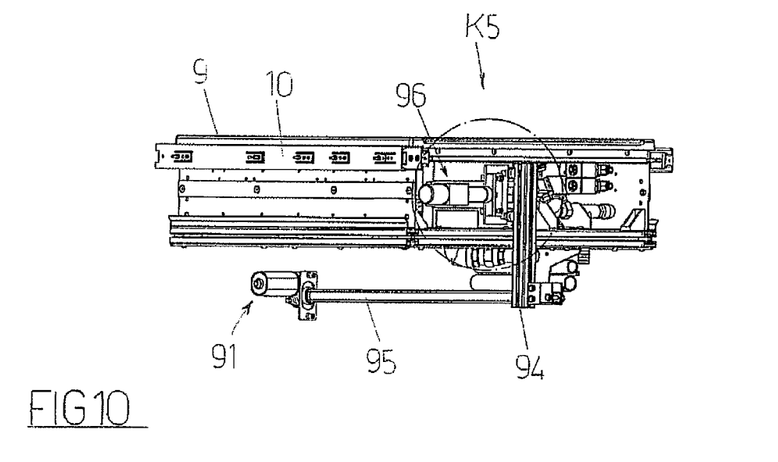
FIG. 10 is the same view as FIG. 9, where further parts have been omitted.

Thus, the activating of the first motor (91) can move the first lateral wall (11) between the first opening (5), see FIGS. 8, 10, in which the first tubular element (95) surrounds the first screw (92), and the first endrun (A1), see FIGS. 6, 6A, 7, 9, 11, where the first tubular element (95) projects with respect to the first screw (92). Therefore the first tubular element (95) can slid along the first screw (92) telescopically by effect of the activating of the first motor (91), and consequently can draw the first lateral wall (11) in the sliding direction (W), between the first opening (5) and the first endrun (A1).

By way of example, the first fixing means (96, 97, 98) comprising: a first linear actuator (96) borne by the bath group (9, 10), which first linear actuator (96) moves a first stem (100) between a disengaged position (FIG. 10A) and an engaged position (FIG. 11A); a first engaging member (97) borne by the first stem (100); a second engaging member (98) borne by the first upright (94).

Figure 10A:
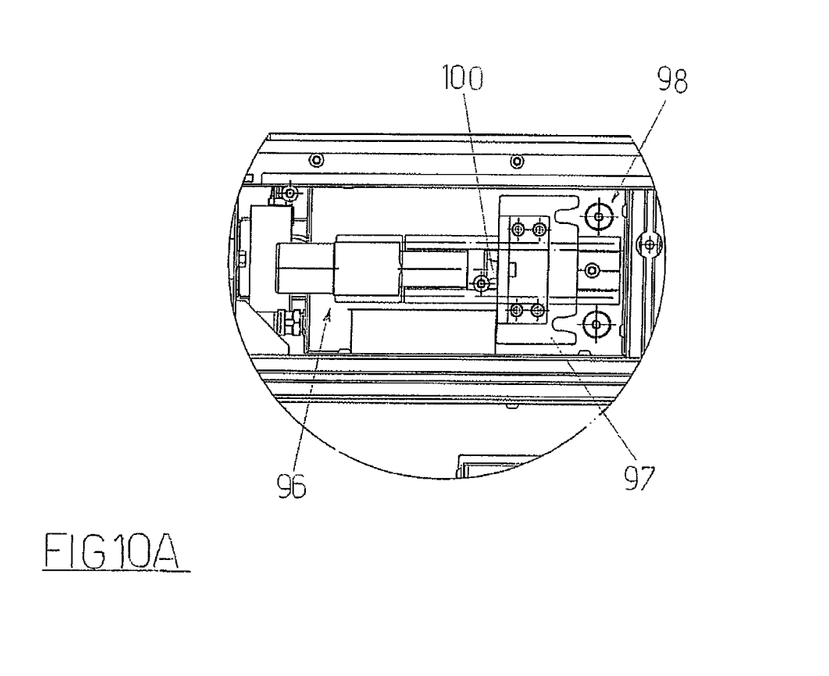
FIG. 10A is a front view in larger scale of detail K5 of FIG. 10, where some parts have been omitted.
Figure 11:
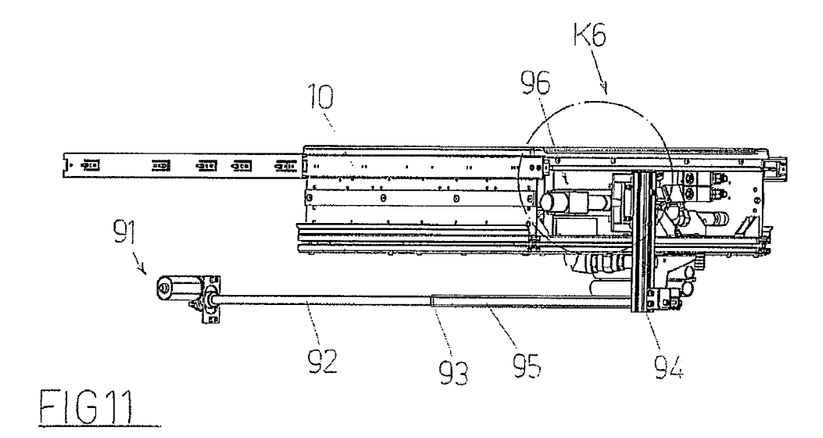
FIG. 11 is the same view as FIG. 10, but where the disinfecting/sterilising machine is in the first service configuration or in the second service configuration.
Figure 11A:
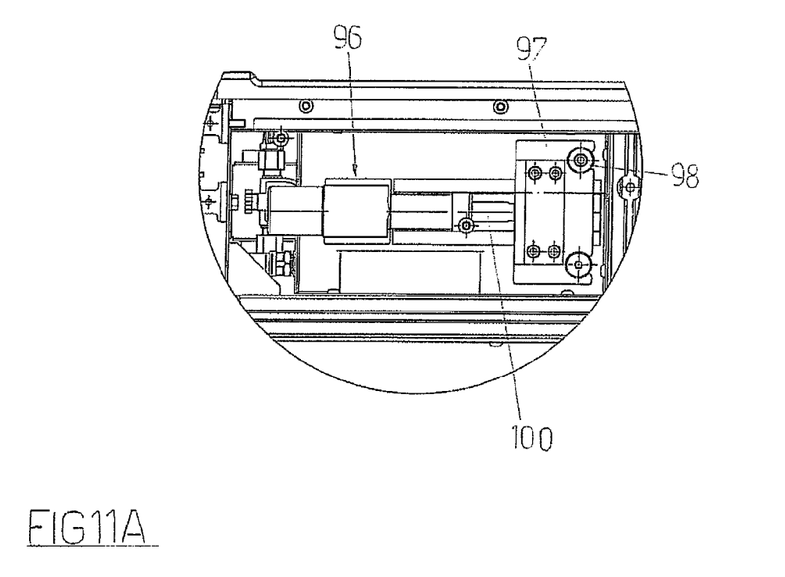
FIG. 11A is a front view in larger scale of detail K6 of FIG. 11, where some parts have been omitted.

In FIGS. 10A, 11A, the upright (94) has not been represented in order better to illustrate the first engaging member (97) and the second engaging member (98).

When the first lateral wall (11) is at the first opening (5) and the bath group (9, 10) is in the tunnel (FIG. 8), the activating of the first stem (100) from the disengaged position (FIG. 10A) to the engaged position (FIG. 11A) determines the coupling of the first engaging member (97) with the second engaging member (98), which makes the bath group (9, 10) solid with the first lateral wall (11) and enables, by the activating of the first motor (91), the movement of the bath group (9, 10) and the first lateral wall (11) towards the first endrun (A1), and vice versa. Once the bath group (9, 10) has returned into the tunnel (4) and first lateral wall (11) is at the first opening (5), the activating of the first stem (100) from the engaged position to the disengaged position deconstrains the bath group (9, 10) from the first lateral wall (11). In this position, the first lateral wall (11) obstructs the first opening (5) and is coupled to the frame (2) of the disinfecting/sterilizing machine (1) by the connection with the first upright (94), the first tubular element (95), the first nutscrew (93), the first screw (92) and the first motor (91).

The disinfecting/sterilising machine (1) can further comprise: a second motor (not illustrated) which is borne by the frame (2); a second screw (not illustrated) that is drawn in rotation by the second motor; a second nutscrew (not illustrated) that engages helically with the second screw so as to translate along the second screw; a second connecting member (not illustrated) which connects the second nutscrew with the second lateral wall (12), second fixing means (not illustrated) for removably fixing the second lateral wall (12) to the bath group (9, 10) when the second lateral wall (12) is at the second opening (6) and the bath group (9, 10) is in the tunnel (4), the second motor, the second screw, the second nutscrew and the second connecting member being dimensioned and arranged with respect to one another such as to enable the bath group (9, 10) to reach the second endrun (A2).

The second screw is preferably orientate parallel to the sliding direction (W).

The second connecting member can comprise: a second upright (not illustrated) that is fixed to the second lateral wall (12); and a second tubular element (not illustrated) which at a third end is fixed to the second upright and which at a forth end is fixed to the second nutscrew, which second tubular element is concentric with the second screw and is dimensioned such as to at least partly contain the second screw internally thereof.

Therefore, the activating of the second motor can move the second lateral wall between the second opening and the second endrun (A2) in which the second tubular element projects with respect to the second screw. Thus, the second tubular element can slide along the second screw telescopically by effect of the activating of the second motor, and consequently can draw the second lateral wall in the sliding direction (W), between the second opening (6) and the second endrun (A2).

By way of example, the second fixing means comprise: a second linear actuator (not illustrated) borne by the bath group (9, 10), which second linear actuator (96) moves a second stem (not illustrated) between a disengaged position and an engaged position; a third engaging member (not illustrated) borne by the second stem; a fourth engaging member borne by the second upright.

When the second lateral wall (12) is at the second opening (6) and the bath group (9, 10) is in the tunnel (FIG. 8), the activating of the second stem from the disengaged position to the engaged position determines the coupling of the third engaging member with the fourth engaging member, which makes the bath group (9, 10) solid with the second lateral wall (12) and enables, by the activating of the second motor (91), the movement of the bath group (9, 10) and the second lateral wall (11) towards the second endrun (A1), and vice versa. Once the bath group (9, 10) has returned into the tunnel (4) and second lateral wall (12) is at the second opening (6), the activating of the second stem (100) from the engaged position to the disengaged position deconstrains the bath group (9, 10) from the second lateral wall (12). In this position, the second lateral wall (12) obstructs the second opening (6) and is coupled to the frame (2) of the disinfecting/sterilizing machine (1) by the connection with the second upright, the second tubular element, the second nutscrew (93), the second screw (92) and the second motor (91).

The disinfecting/sterilising machine (1) preferably comprises: a control unit (not illustrated); a user interface (101) connected to the control unit, so as to provide commands of a user to the control unit; the control unit in turn commanding the first motor (91), the second motor, the first fixing means (96, 97, 98) and the second fixing means.

The user interface (101) can be a keyboard with a monitor, or a touch-screen.

The user (101) can use the interface to manage the functioning of the disinfecting/sterilising machine (1), for example by electrically commanding the movement of the bath group (9, 10) from the tunnel (4) towards the first endrun (A1) or towards the second endrun (A2).

It is understood that the foregoing has been described by way of non-limiting example, and any constructional variant are understood to fall within the protective scope of the present technical solution, as claimed in the following.

The invention claimed is:

1. A disinfecting or sterilizing machine for disinfecting or sterilizing endoscopes, comprising:
   a frame;
   a casing covering the frame;
   the frame and the casing being conformed with respect to one another such as to define at least a tunnel having a first opening and a second opening which is opposite the first opening;
   an upper wall which at least partially superiorly delimits the tunnel;
   a first lateral wall positionable at the first opening such as to obstruct the tunnel; and
   a second lateral wall positionable at the second opening such as to obstruct the tunnel,
   the disinfecting or sterilizing machine further comprising:
   a bath dimensioned such as to receive at least an endoscope to disinfect or sterilize and which is dimensioned such as to transit along the tunnel;
   a bath support fixed to the bath, the bath support and the bath forming a bath group; and
   guide means for guiding the bath group along the tunnel between: a first endrun in which the bath projects externally from the first opening of the tunnel such as to be accessible for inserting or extracting the at least an endoscope and a second endrun in which the bath projects externally from the second opening of the tunnel such as to be accessible for inserting or extracting the at least an endoscope, wherein:
the upper wall forms, with the bath, a closed chamber such as to disinfect or sterilize the at least an endoscope when the bath is internal of the tunnel;
the first lateral wall, when at the first opening, is couplable alternatively and removably with the frame, such as to be solidly constrained to the frame and obstruct the tunnel or with the bath support such as to be solidly constrained to and be drawn by the bath group and enable the bath group to reach the first endrun; and
the second lateral wall, when at the second opening, is alternatively and removably couplable with the frame, such as to be solidly constrained to the frame and obstruct the tunnel or with the bath support such as to be solidly constrained to and be drawn by the bath group and enable the bath group to reach the second endrun.

2. The disinfecting or sterilizing machine of claim 1, further comprising:
a first mechanism carried by the first lateral wall and activatable, when the first lateral wall is at the first opening, between a first operative configuration in which it interacts with the frame such as to anchor the first lateral wall to the frame, and a second operative configuration, in which it interacts with the bath support such as to anchor the first lateral wall to the bath support when the bath group is in the tunnel; and
a first handle which is carried by the first lateral wall, which is rotatable between a first angular position and a second angular position and which is couplable to the first mechanism such that when the first handle is activated into the first angular position, the first mechanism reaches the first operative configuration, and when the first handle is activated into the second angular position, the first mechanism reaches the second operative configuration.

3. The disinfecting or sterilizing machine of claim 2, comprising a second mechanism borne by the second lateral wall and activatable, when the second lateral wall is at the second opening, between a third operative configuration, in which it interacts with the frame such as to anchor the second lateral wall to the frame, and a fourth operative configuration, in which it interacts with the bath support such as to anchor the second lateral wall to the bath support when the bath group is in the tunnel; and
a second handle which is borne by the second lateral wall, which is rotatable between a third angular position and a fourth angular position and which is couplable to the second mechanism such that when the second handle is activated into the third angular position the second mechanism reaches the third operative configuration and when the second handle is activated into the fourth angular position the second mechanism reaches the fourth operative configuration.

4. The disinfecting or sterilizing machine of claim 2, wherein the first handle and the first mechanism are on a side of the first lateral wall which is opposite the side where the bath group is located:
wherein the first lateral wall affords a through-hole;
wherein the bath support bears a first projecting element having a first head, which first projecting element is dimensioned such as to be inserted through the through-hole and such as to project therefrom by the first head when the bath group is in the tunnel and the first lateral wall is at the first opening;
wherein the first mechanism comprises: a first member fixed to the first handle, which first member forms a first coupling seating which engages with the first head of the first projecting element when the first handle is in the second angular position, when the first lateral wall is at the first opening and when the bath group is in the tunnel, determining the anchoring of the first lateral wall to the bath support.

5. The disinfecting or sterilizing machine of claim 4, wherein the first mechanism further comprises: a first latch activatable between an advanced position and a retracted position following the movement of the first handle respectively between the first angular position and the second angular position; wherein the frame comprises a first blocking seating for receiving the first latch when the first latch reaches the advanced position and when the first lateral wall is at the first opening, with a consequent anchoring of the first lateral wall to the frame.

6. The disinfecting or sterilizing machine of claim 3, wherein the second handle and the second mechanism are on a side of the second lateral wall which is opposite the side where the bath group is located:
wherein the second lateral wall affords a through-hole;
wherein the bath support bears a second projecting element having a second head, which second projecting element is dimensioned such as to insert through the through-hole and to project therefrom by the second head when the bath group is in the tunnel and the second lateral wall is at the second opening;
wherein the second mechanism comprises: a second member fixed to the second handle, which second member forms a second coupling seating which engages with the second head of the second projecting element when the second handle is in the second angular position, when the second lateral wall is at the second opening and when the bath group is in the tunnel, determining the anchoring of the second lateral wall to the bath support.

7. The disinfecting or sterilizing machine of any claim 3, wherein the second mechanism further comprises: a second latch activatable between an advanced position and a retracted position following the movement of the second handle respectively between the third angular position and the fourth angular position;
wherein the frame comprises a second blocking seating for receiving the second latch when the second latch reaches the advanced position and when the second lateral wall is at the second opening, with a consequent anchoring of the second lateral wall to the frame.

8. The disinfecting or sterilizing machine of claim 1, further comprising:
a first motor which is borne by the frame;
a first screw which is drawn in rotation by the first motor;
a first nutscrew which engages helically with the first screw so as to translate along the first screw;
a first connecting member which connects the first nutscrew with the first lateral wall;
first fixing means for removably fixing the first lateral wall to the bath group when the first lateral wall is at the first opening and the bath group is in the tunnel, the first motor, the first screw, the first nutscrew and the first connecting member being dimensioned and arranged with respect to one another so as to enable the bath group to reach the first endrun.

9. The disinfecting or sterilizing machine of claim 8, wherein the first connecting member comprises: a first upright which is fixed to the first lateral wall; and a first tubular element which is fixed at a first end to the first upright and which at a second end is fixed to the first nutscrew, which first tubular element is concentric with the first screw and is dimensioned such as to at least partly contain the first screw internally thereof.

10. The disinfecting or sterilizing machine of claim 8, further comprising:
    a second motor which is borne by the frame;
    a second screw that is drawn in rotation by the second motor;
    a second nutscrew that engages helically with the second screw so as to translate along the second screw;
    a second connecting member which connects the second nutscrew with the second lateral wall; and
    second fixing means for removably fixing the second lateral wall to the bath group when the second lateral wall is at the second opening and the bath group is in the tunnel, the second motor, the second screw, the second nutscrew and the second connecting member being dimensioned and arranged with respect to one another such as to enable the bath group to reach the second endrun.

11. The disinfecting or sterilizing machine of claim 10, wherein the second connecting member comprises:
    a second upright that is fixed to the second lateral wall; and
    a second tubular element which at a third end is fixed to the second upright and which at a forth end is fixed to the second nutscrew, which second tubular element is concentric with the second screw and is dimensioned such as to at least partly contain the second screw internally thereof.

12. The disinfecting or sterilizing machine of claim 10, comprising:
    a control unit; and
    a user interface connected to the control unit, so as to provide a user's commands to the control unit;
    the control unit in turn commanding the first motor, the second motor, the first fixing means and the second fixing means.

13. The disinfecting or sterilizing machine of claim 12, comprising a seal which:
    is borne by the upper wall; develops in a closed loop such as to face the perimeter edge of the bath when the bath is in the tunnel;
    has a tubular transversal section for containing a pressurized fluid;
    is made of a material which enables the seal to expand or retract according to the fluid pressure contained internally thereof;
    is dimensioned such that when it expands and when the bath is in the tunnel the chamber is hermetically closed; and
    is dimensioned such that when it retracts the bath group can transit freely through the tunnel.

\* \* \* \* \*